US006232315B1

(12) United States Patent
Shafer et al.

(10) Patent No.: US 6,232,315 B1
(45) Date of Patent: May 15, 2001

(54) METHOD FOR TREATING INFLAMMATORY DISEASES BY ADMINISTERING A THROMBIN INHIBITOR

(75) Inventors: Jules Shafer, Gwynedd Valley, PA (US), .; Denise M. Visco, Fanwood, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/407,821

(22) Filed: Sep. 28, 1999

Related U.S. Application Data

(60) Provisional application No. 60/102,020, filed on Sep. 28, 1998.

(51) Int. Cl.$^7$ .................. A61K 31/341; A61K 31/4412; A61K 31/454; A61K 31/497
(52) U.S. Cl. .................... 514/255.05; 514/326; 514/334; 514/473
(58) Field of Search ............................. 514/255.05, 326, 514/473, 334

(56) References Cited

FOREIGN PATENT DOCUMENTS

97/16405 * 5/1997 (WO) .

OTHER PUBLICATIONS

Tapparelli et al., TiPS (14) 366–376, OCt. 1993.*
Halpern, B., et al., "Protective Action of Heparin in Experimental Immune Nephritis," *NATURE*, No. 4968, pp. 257–259, (Jan. 16, 1965).
Sherman, L. A., et al., "Specific Binding of Soluble Fibrin to Macrophages," *J. Experimental Med.*, vol. 145, pp. 76–85, (1977).
Cole, E. H., et al., "Monocyte Procoagulant Activity in Glomerulonephritis Associated with Systemic Lupus Erythematosus," *J. Clin. Invest.*, vol. 75, pp. 861–868, (Mar. 1985).
Altieri, D.C., et al., "Binding of Fibrinogen to Human Monocytes," *J. Clin. Invest.*, vol. 78, pp. 968–976, (Oct. 1986).
Naish, P., et al., "The Effect of Defibrination on Nephrotoxic Serum Nephritis in Rabbits," *Clinical Science*, vol. 42, pp. 643–646, (1972).
Kincaid–Smith, Priscilla, "Coagulation and Renal Disease," *Kidney International*, vol. 2, pp. 183–190, (1972).
Kim, S., et al., "Fibrinoloysis in Glomerulonephritis Treated With Ancrod: Renal Functional, Immunologic and Histopathologic Effects ," *Quarterly Journal of Medicine* New Series 69, No. 259, pp. 879–895. (Nov. 1988).
Jasani, M.K., "Fibrin: Metabolism, Immunopathogenesis and Significance in Rheumatoid Arthritis," *Immunopathogenesis of Rheumatoid Arthritis*, pp. 137–146.
Busso, N., et al., "Exacerbation of Antigen–induced Arthritis in Urokinase–deficient Mice," *J. Clin. Invest.*, vol. 102, No. 1, pp. 41–50, (Jul. 1998).

Zacharski, L.R., et al., "Pathways of Coagulation Activation in Situ in Rheumatoid Synovial Tissue," *Clinical Immunology and Immunopathology*, vol. 63, No. 2, pp. 155–162, (May 1992).
Altieri, D.C., et al., "The Structural Motif Glycine 190–Valine 202 of the Fibrinogen Chain Interacts with CD11b/CD18 Integrin( mB2,) Mac–1 and Promotes Leukocyte Adhesion," *Journal of Biological Chemistry*, vol. 268, No. 3, Issue of Jan. 25, pp. 1847–1853, (1993).
Perez, R.L., et al., "Fibrin Enhances the Expression of IL–1 by Human Peripheral Blood Mononuclear Cells (Implications in Pulmonary Inflammation), " *Journal of Immunology*, vol. 154, pp. 1879–1887, 1995.
Cole, E.H., et al., "Ancrod Improves Survival in Murine Systemic Lupus Erythematosus," *Kidney International*, vol. 37, pp. 29–35, 1990.
Wright, S.D., et al., "Complement Receptor Type Three (CD 11b/CD18) of Human Polymorphonuclear Leukocytes Recognizes Fibrinogen," *Proc. Natl. Acad. Sci. USA*, vol. 85, Immunology, pp. 7734–7738, (Oct. 1988).

* cited by examiner

*Primary Examiner*—Phyllis G. Spivack
(74) *Attorney, Agent, or Firm*—Richard S. Parr; Melvin Winokur

(57) ABSTRACT

The invention is a method for treating an inflammatory disease in a patient which comprises treating the patient with a composition comprising a thrombin inhibitor. Such diseases include but are not limited to nephritis, systemic lupus erythematosus, rheumatoid arthritis, glomerulonephritis, and sacoidosis. In one class of the method, the thrombin inhibitor is selected from the group consisting of 3-(2-phenylethylamino)-6-methyl-1-(2-amino-6-methyl-5-methylenecarboxamidomethylpyridinyl)-2-pyrazinone, N'-[[1-(aminoiminomethyl)-4-piperidinyl]methyl]-N-(3,3-diphenylpropionyl)-L-proline amide, and 3-(2-phenethylamino)-6-methyl-1-(2-amino-6-methyl-5-methylenecarboxamidomethylpyridinyl)-2-pyridinone or a pharmaceutically acceptable salt thereof.

The invention is also a method for treating an inflammatory disease in a patient which comprises treating the patient with a composition comprising a thrombin inhibitor and an NSAID, e.g., a COX-2 inhibitor. Such diseases include but are not limited to nephritis, systemic lupus, erythematosus, rheumatoid arthritis, glomerulonephritis, and sacoidosis. In one class of the method, the thrombin inhibitor is selected from the group consisting of 3-(2-phenylethylamino)-6-methyl-1-(2-amino-6-methyl-5-methylene-carboxamidomethylpyridinyl)-2-pyrazinone, N'-[[1-(aminoiminomethyl)-4-piperidinyl]methyl]-N-(3,3-diphenylpropionyl)-L-proline amide, and 3-(2-phenethylamino)-6-methyl-1-(2-amino-6-methyl-5-methylenecarboxamidomethylpyridinyl)-2-pyridinone or a pharmaceutically acceptable salt thereof and the COX-2 inhibitor is 3-phenyl-4-(4-(methylsulfonyl)phenyl)-2-(5H)-furanone or a pharmaceutically acceptable salt thereof.

7 Claims, No Drawings

METHOD FOR TREATING INFLAMMATORY DISEASES BY ADMINISTERING A THROMBIN INHIBITOR

This application claims benefit of Provisional application Ser. No. 60/102 020 filed Sep. 28, 1998.

BACKGROUND OF THE INVENTION

This invention relates to methods for treating inflammatory diseases by administration of a thrombin inhibitor.

Anti-inflammatory drugs include non steroidal anti-inflammatory drugs (NSAIDs) which exert anti-inflammatory, analgesic and antipyretic activity. These include salicylates such as aspirin, sodium salicylate, choline salicylate, salicylsalicylic acid, diflunisal, and salsalate; indoleacetic acids such as indomethacin and sulindac; pyrazoles such as phenylbutazone, oxyphenbutazone; pyrroleal-kanoic acids such as tolmetin; phenylacetic acids such as ibuprofen, feroprofen, flurbiprofen, and ketoprofen; fenamates such as mefanamic acid, and meclofenamate; oxicams such as piroxicam; and naphthaleneacetic acids such as naproxen. Nearly all act by inhibiting cyclo-oxygenase activity. Aspirin, for example, acetylates and irreversibly inactivates cyclo-oxygenase. Others, such as indomethacin, inhibit cyclo-oxygenase activity reversibly by binding in a stereospecific manner to one or another subunit of the enzyme. NSAIDs are active in reducing the prostaglandin-induced pain and swelling associated with the inflammation process but are also active in affecting other prostaglandin-regulated processes not associated with the inflammation process. Thus, use of high doses of most common NSAIDs can produce severe side effects, including life threatening ulcers, that limit their therapeutic potential.

Adrenal corticosteroids, which are alternatives to NSAIDs for treating inflammatory diseases, have even more drastic side effects, especially when long term therapy is involved. These steroids, including hydrocortisone, prednisolone, 6 alpha-methylprednisolone, triamcinolone, dexamethasone and betaroethasone, affect inflammation by a possible mechanism whereby they bind to intracellular glucocorticoid receptors to subsequently initiate a series of cellular events involving synthesis of new phospholipid inhibitory proteins, or lipocortins, that can affect the inflammatory and the teratogenic responses of certain cells exposed to glucocorticoids. The anti-inflammatory effect of glucocorticoids has been well documented.

Excessive bleeding disorders are associated with development of inflammatory conditions. Hemophilia, a bleeding disorder caused by a deficiency clotting Factor VIII or clotting Factor IX, can result in recurring bleeding into joints and muscles that causes crippling inflammation and deformities. Hemophilia also causes swelling of the base of the tongue until it blocks the airway.

Thrombin inhibitors are known to be useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood, but have not been recognized as useful for treating inflammatory diseases.

As described below, it has now been found that thrombin inhibitors, which inhibit formation of blood clots, are in fact effective for inhibiting inflammation.

SUMMARY OF THE INVENTION

The invention is a method for treating an inflammatory disease in a patient which comprises treating the patient with a composition comprising a thrombin inhibitor. Such diseases include but are not limited to nephritis, systemic lupus erythematosus, rheumatoid arthritis, glomerulonephritis, and sacoidosis. In one class of the method, the thrombin inhibitor is selected from the group consisting of 3-(2-phenylethylamino)-6-methyl-1-(2-amino-6-methyl-5-methylene-carboxamidomethylpyridinyl)-2-pyrazinone, N'-[[1-(Aminoiminomethyl)-4-piperidinyl]methyl]-N-(3,3-diphenylpropionyl)-L-proline amide, and 3-(2-phenethylamino)-6-methyl-1-(2-amino-6-methyl-5-methylenecarboxamidomethylpyridinyl)-2-pyridinone or a pharmaceutically acceptable salt thereof.

The invention is also a method for treating an inflammatory disease in a patient which comprises treating the patient with a combination comprising a thrombin inhibitor and an NSAID, e.g., a COX-2 inhibitor. Such diseases include but are not limited to nephritis, systemic lupus, erythematosus, rheumatoid arthritis, glomerulonephritis, vasculitis and sarcoidosis. In one class of the method, the thrombin inhibitor is selected from the group consisting of 3-(2-phenylethylamino)-6-methyl-1-(2-amino-6-methyl-5-methylene-carboxamidomethylpyridinyl)-2-pyrazinone, N'-[[1-(Aminoiminomethyl)-4-piperidinyl]methyl]-N-(3,3-diphenylpropionyl)-L-proline amide, and 3-(2-phenethylamino)-6-methyl-1-(2-amino-6-methyl-5-methylenecarboxamidomethylpyridinyl)-2-pyridinone or a pharmaceutically acceptable salt thereof and the COX-2 inhibitor is selected from the group consisting of 3-phenyl-4-(4-(methylsulfonyl)phenyl)-2-(5H)-furanone and 3-(3,4-difluorophenyl)-4-(4-(methylsulfonyl)phenyl)-2-(5H)-furanone, or a pharmaceutically acceptable salt thereof.

The invention is also a method for inhibiting secondary inflammation in a patient developing inflammation at a primary site which comprises treating the patient with a composition comprising a thrombin inhibitor. Such inhibited secondary inflammation is inflammation that would otherwise occur in an untreated patient resulting from inflammatory diseases in which fibrin serves as a matrix onto which inflammatory cells migrate and adhere.

DETAILED DESCRIPTION OF THE INVENTION

The present invention is a method for relieving pain, fever and inflammation of a variety of conditions including nephritis, systemic lupus erythematosus, rheumatoid arthritis, glomerulonephritis, sacoidosis, rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursitis, bums, injuries, following surgical and dental procedures in a patient by administering to the patient a therapeutically effective amount of a thrombin inhibitor. Thrombin inhibitors may also be useful for the treatment of dementia including pre-senile and senile dementia, and in particular, dementia associated with Alzheimer Disease.

In inflammatory diseases wherein fibrin formation is prominent, the fibrin may be a determinant of the pathology.

Fibrin serves as a matrix onto which inflammatory cells can migrate and adhere. (see Sherman et al., 1977 *J. Exp. Med.* 145:76–85; Altieri et al., 1986 *J. Clin. Invest.* 78:968–976; Wright et al., 1983 *Proc. Natl. Acad. Sci.* 85:7734–7738; Altieri et al., 1993 *J. Biol. Chem.* 268;1847–1853). Fibrin also enhances expression of the inflammatory cytokine IL-1beta and decreases expression of IL-1 receptor antagonist by human peripheral blood mononuclear cells (see Perez 1995 *J. Immunol.* 154:1879–1887). The anticoagulants warfarin and heparin attenuate delayed-type hypersensitivity reactions and experimental nephritis in animals. (see Jasain et al., Immunopathogenesis of Rheumatoid Arthritis Eds. G. S. Panayi et al., Surrey, UK, Reedbooks, Ltd. and Halpern et al., 1965 *Nature* 205:257–259). Enzymatic defibrination with ancrod diminishes the degree of experimental nephritis (Naish et al., 1972 *Clin. Sci.* 42:643–646), systemic lupus erythematosus (Cole et al., 1990 *Kidney Int.* 37:29–35, and rheumatoid arthritis (see Busso et al., 1998 *J. Clin. Invest.* 102:41–50) in animals, and glomerulonephritis in man (see Kim et al., 1988 *O. J. Med.* 69:879–905). Additionally, intra articular injection of fibrin induces arthritis in rabbits immunized with fibrin Dumonde et al., 1961 *British Journal of Experimental Pathology XLIII:*373–383), and antigen-induced arthritis in mice is exacerbated in urokinase-deficient mice wherein fibrinolysis synovial fibrin is compromised (see Busso et al., 1998 *J. Clin. Invest.* 102:41–50).

In diseases where fibrin deposition is prominent such as, but not limited to, rheumatoid arthritis, systemic lupus erythematosus, glomerulonephritis, vasculitis and sacoidosis, lowering the steady state concentration of fibrin by administration of a direct thrombin inhibitor will, according to the instant invention, diminish the pathological inflammatory responses associated with these diseases.

Thrombin inhibitors

Thrombin inhibitors are compounds which inhibit hydrolytic activity of thrombin, including the catalytic conversion of fibrinogen to fibrin, activation of Factor V to Va, Factor VIII to VIIIa, Factor XIII to XIIIa, and activation of platelets.

Compounds may be identified as thrombin inhibitors by evaluating the compounds in assays described in S. D. Lewis et al., *Thrombosis Research* 70 pp. 173–190 (1993). One assay involves the measurement of rates of substrate hydrolysis, and the other involves measurement of activated partial thromboplastin time.

Hydrolysis assays may be carried out at 25° C. in 0.05 M TRIS buffer pH 7.4, 0.15 M NaCl, 0.1 % PEG. Trypsin assays may also contain 1 mM CaCl2. In assays wherein rates of hydrolysis of a p-nitroanilide (pna) substrate are determined, a Thermomax 96-well plate reader is used to measure (at 405 nm) the time dependent appearance of p-nitroaniline. sar-PR-pna is used to assay human α-thrombin ($K_m$=125 µM) and bovine trypsin ($K_m$=125 µM). p-Nitroanilide substrate concentration is determined from measurements of absorbance at 342 nm using an extinction coefficient of 8270 cm$^{-1}$M$^{-1}$.

In certain studies with potent inhibitors ($K_i$<10 nM) where the degree of inhibition of thrombin is high, a more sensitive activity assay may be used. In this assay, the rate of thrombin catalyzed hydrolysis of the fluorogenic substrate Z-GPR-afc ($K_m$=27 µM) is determined from the increase in fluorescence at 500 nm (excitation at 400 nm) associated with production of 7-amino4-trifluoromethyl coumarin. Concentrations of stock solutions of Z-GPR-afc are determined from measurements of absorbance at 380 nm of the 7-amino-4-trifluoromethyl coumarin produced upon complete hydrolysis of an aliquot of the stock solution by thrombin.

Activity assays are performed by diluting a stock solution of substrate at least tenfold to a final concentration $\leq$0.1 $K_m$ into a solution containing enzyme or enzyme equilibrated with inhibitor. Times required to achieve equilibration between enzyme and inhibitor are determined in control experiments. Initial velocities of product formation in the absence ($V_o$) or presence of inhibitor ($V_i$) are measured. Assuming competitive inhibition, and that unity is negligible, $K_m$/[S], [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in equation 1.

$$V_o/V_i=1+[I]/K_i \tag{1}$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels. The compounds of the invention are selective compounds, as evidenced by their inhibitory activity against human trypsin (represented by Ki), which is at least 1000 nM.

The anticoagulant effect of thrombin inhibitors can be verified according to the activated partial thromboplastin time assay described by S. D. Lewis et al., *Thrombosis Research* 70 pp. 173–190 (1993). According to the assay, citrated plasma is mixed with the test compound and with activated cephaloplastin reagent. Calcium chloride is then added to the mixture, and the degree of coagulation is measured. The absence of coagulation demonstrates the inability of the test compound to inhibit thrombin.

Thrombin inhibitors suitable for the present invention include those which inhibit thrombosis, including but not limited to those described in U.S. Pat. No. 5,536,708, U.S. Pat. No. 5,510,369, U.S. Pat. No. 5,672,582, U.S. Pat. No. 5,714,485, U.S. Pat. No. 5,629,324 (e.g. N'-[[1-(Aminoiminomethyl)-4-piperidinyl]methyl]-N-(3,3-diphenylpropionyl)-L-proline amide), U.S. Pat. No. 5,668,289 (e.g. 3-(2-Phenethylamino)-6-methyl- 1 -(2-amino-6-methyl-5-methylenecarboxamidomethylpyridinyl)-2-pyridinone), U.S. Pat. No. 5,744,486, U.S. Pat. No. 5,798,377, WO 9631504, WO 9611941, WO 9606832, WO 9606849, WO9420467, WO 9632110, U.S. Pat. No. 4,496,653, WO 9715190, and WO 9740024, e.g. 3-(2-Phenylethylamino)-6-methyl- 1-(2-amino-6-methyl-5-methylene-carboxamidomethylpyridinyl)-2-pyrazinone, the contents of which are hereby incorporated by reference. Such compounds are known to be useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025–7.5 mg/kg/day, more preferably 0.1–2.5 mg/kg/day, and most preferably 0.1–1.0 mg/kg/day (unless specified otherwise, amounts of active ingredients are on free base basis). For example, an 80 kg patient would receive between about 0.8 mg/day and 2.4 g/day, preferably 2–600 mg/day, more preferably 8–200 mg/day, and most preferably 8–80 mg/day. A suitably prepared medicament for once a day administration would thus contain between 0.8 mg and 2.4 g, preferably between 2 mg and 600 mg, more preferably between 8 mg and 200 mg, and most preferably 8 mg and 80 mg, e.g., 8 mg, 20 mg, 40 mg and 80 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 40 mg, e.g., 4 mg, 10 mg, 20 mg and 40 mg.

Intravenously or subcutaneously, the patient would receive the active ingredient in quantities sufficient to deliver between 0.025–7.5 mg/kg/day, preferably 0.1–2.5 mg/kg/day, and more preferably 0.1–1.0 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. Consideration should be given to the solubility and chemical compatibility of the drug in choosing an appropriate excipient. Subcutaneous formulations, preferably prepared according to procedures well known in the art at a pH in the range between 7.0 and 7.4, also include suitable buffers and isotonicity agents. They are formulated to deliver a daily dose of thrombin inhibitor in one or more daily subcutaneous administrations, e.g., one, two or three time each day. The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

Typical uncoated tablet cores suitable for administration of thrombin inhibitors are comprised of, but not limited to, the following amounts of standard ingredients:

| Excipient | General Range (%) | Preferred Range (%) | Most Preferred Range (%) |
|---|---|---|---|
| mannitol | 10–90 | 25–75 | 30–60 |
| microcrystalline cellulose | 10–90 | 25–75 | 30–60 |
| magnesium stearate | 0.1–5.0 | 0.1–2.5 | 0.5–1.5 |

Mannitol, microcrystalline cellulose and magnesium stearate may be substituted with alternative pharmaceutically acceptable excipients.

All of the thrombin inhibitor, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

The examples are merely illustrative and should not be interpreted as limiting the scope of the claimed invention.

EXAMPLE 1

Tablet Preparation

Exemplary thrombin inhibitor tablet compositions include those shown below where the thrombin inhibitor is 3-(2-phenylethylamino)-6-methyl-1-(2-amino-6-methyl-5-methylene-carboxamidomethylpyridinyl)-2-pyrazinone, N'-[[1-(aminoiminomethyl)-4-piperidinyl]methyl]-N-(3,3-diphenylpropionyl)-L-proline amide, or 3-(2-phenethylamino)-6-methyl-1-(2-amino-6-methyl-5-methylenecarboxamidomethylpyridinyl)-2-pyridinone:

| Component | 0.25 mg | 2 mg | 10 mg | 50 mg |
|---|---|---|---|---|
| thrombin inhibitor | 0.500% | 1.000% | 5.000% | 14.29% |
| mannitol | 49.50% | 49.25% | 47.25% | 42.61% |
| microcrystalline cellulose | 49.50% | 49.25% | 47.25% | 42.61% |
| magnesium stearate | 0.500% | 0.500% | 0.500% | 0.500% |

2, 10 and 50 mg tablets were film-coated with an aqueous dispersion of hydroxypropyl cellulose, hydroxypropyl methylcellulose and titanium dioxide, providing a nominal weight gain of 2.4%.

Tablet preparation via direct compression

The thrombin inhibitor, mannitol and microcrystalline cellulose were sieved through mesh screens of specified size (generally 250 to 750 m) and combined in a suitable blender. The mixture was subsequently blended (typically 15 to 30 min) until the drug was uniformly distributed in the resulting dry powder blend. Magnesium stearate was screened and added to the blender, after which a precompression tablet blend was achieved upon additional mixing (typically 2 to 10 min). The precompression tablet blend was then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets were dedusted and film-coated with an aqueous dispersion of water-soluble polymers and pigment.

Tablet preparation via dry granulation

Alternatively, a dry powder blend is compacted under modest forces and remilled to afford granules of specified particle size. The granules are then mixed with magnesium stearate and tabletted as stated above

EXAMPLE 2

Intravenous Formulations

Exemplary thrombin inhibitor intravenous formulations, prepared according to general intravenous formulation procedures, are those shown below where the thrombin inhibitor is 3-(2-phenylethylamino)-6-methyl-1-(2-amino-6-methyl-5-methylene-carboxamidomethylpyridinyl)-2-pyrazinone, N'-[[1-(aminoiminomethyl)-4-piperidinyl]methyl]-N-(3,3-diphenylpropionyl)-L-proline amide, or 3-(2-phenethylamino)-6-methyl-1-(2-amino-6-methyl-5-methylenecarboxamidomethylpyridinyl)-2-pyridinone:

| Component | Estimated range |
|---|---|
| Thrombin inhibitor | 0.1–1.2 mg |
| D-glucuronic acid* | 0.5–5 mg |
| Mannitol NF | 50–53 mg |
| Water for injection | q.s. 1.0 mL |

1N sodium hydroxide is used to achieve a solution pH in the range of between 3.9–4.1.

Exemplary compositions A–C are as follows:

| Component | A | B | C |
|---|---|---|---|
| Thrombin inhibitor | 1.2 mg* | 0.60** | 0.15*** |
| D-glucuronic acid* | 1.94 mg | 1.94 mg | 1.94 mg |
| Mannitol NF | 51.2 mg | 51.2 mg | 51.2 mg |
| 1 N Sodium Hydroxide | q.s. pH 4.0 | q.s. pH 4.0 | q.s. pH 4.0 |
| Water for injection | q.s. 1.0 mL | q.s. 1.0 mL | q.s. 1.0 mL |

*1.0 mg free base;
**0.5 mg free base;
***0.12 mg free base

Various other buffer acids, such as L-lactic acid, acetic acid, citric acid or any pharmaceutically acceptable acid/conjugate base with reasonable buffering capacity in the pH range acceptable for intravenous administration may be substituted for glucuronic acid.

EXAMPLE 3

Subcutaneous Formulations

Exemplary thrombin inhibitor subcutaneous formulations, prepared according to general subcutaneous formulation procedures, are those shown below where the thrombin inhibitor is 3-(2-phenylethylamino)-6-methyl-1-(2-amino-6-methyl-5-methylene-carboxamidomethylpyridinyl)-2-pyrazinone, N'-[[1-

(aminoiminomethyl)-4-piperidinyl]methyl]-N-(3,3-diphenylpropionyl)-L-proline amide, or 3-(2-phenethylamino)-6-methyl-1-(2-amino-6-methyl-5-methylenecarboxamidomethylpyridinyl)-2-pyridinone:

| Component | |
|---|---|
| Thrombin inhibitor | 25 mg/ml |
| Citric acid buffer | 10 mM |
| Sodium chloride | 5 mg/ml |
| Water for injection | q.s. 1.0 ml |

1N sodium hydroxide is used to achieve a solution pH in the range of between 7.0–7.4.

Phosphate buffers and various other buffer acids, such as L-lactic acid, acetic acid, glucuronic acid or any pharmaceutically acceptable acid/conjugate base with reasonable buffering capacity in the pH range acceptable for subcutaneous administration may be substituted for citric acid.

"Pharmaceutically acceptable salts" means non-toxic salts of the compounds employed in this invention which are generally prepared by reacting the free acid with a suitable organic or inorganic base. Examples of salt forms of thrombin inhibitors may include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, hexylresorcinate, hydrabamine, hydrobromide, hydrochloride, hydroxynapthoate, isothionate, lactate, lactobionate, laurate, malate, maleate, mandelate, mesylate, methylsulfate, mucate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, and valerate. Examples of salt forms of COX-2 inhibitors include but are not limited to salts derived from inorganic bases including aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Unless defined otherwise, "therapeutically effective amount" means that amount of a drug or pharmaceutical agent that will elicit the biological or medical response of a tissue, a system, animal or human that is being sought by a researcher, veterinarian, medical doctor or other clinician.

Unless defined otherwise, "prophylactically effective amount" means that amount of a pharmaceutical drug that will prevent or reduce the risk of occurrence of the biological or medical event that is sought to be prevented in a tissue, a system, animal or human by a researcher, veterinarian, medical doctor or other clinician.

The term "patient" includes mammals, especially humans, who take a thrombin inhibitor in combination with a COX-2 inhibitor for any of the uses described herein.

Similarly, thrombin inhibitors will be useful as a partial or complete substitute for conventional NSAIDs in preparations wherein they are presently co-administered with other agents or ingredients. Thus in further aspects, the invention encompasses pharmaceutical compositions for treating inflammatory diseases as defined above comprising a non-toxic therapeutically effective amount of a thrombin inhibitor as defined above and one or more ingredients such as another pain reliever including acetominophen or phenacetin; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; a diuretic; a sedating or non-sedating antihistamine. In addition the invention encompasses a method of treating inflammatory diseases comprising administration to a patient in need of such treatment a non-toxic therapeutically effect amount of a thrombin inhibitor, optionally co-administered with one or more of such ingredients as listed immediately above.

The instant invention also involves a novel combination therapy comprising the administration of a therapeutically effective amount of an NSAID such as a COX-2 inhibitor in combination with a therapeutically effective amount of a thrombin inhibitor to a mammal, and more particularly, to a human. The combination therapy is used to treat inflammatory diseases.

Combination

The instant pharmaceutical combinations comprising a thrombin inhibitor in combination with an NSAID such as a COX-2 inhibitor include administration of a single pharmaceutical dosage formulation which contains both the thrombin inhibitor and the NSAID, as well as administration of each active agent in its own separate pharmaceutical dosage formulation. Where separate dosage formulations are used, the thrombin inhibitor and the NSAID can be administered at essentially the same time, i.e., concurrently, or at separately staggered times, i.e, sequentially. The "instant pharmaceutical combination" is understood to include all these regimens. Administration in these various ways are suitable for the present invention as long as the beneficial pharmaceutical effect of the thrombin inhibitor and the NSAID are realized by the patient at substantially the same time. Such beneficial effect is preferably achieved when the target blood level concentrations of each active drug are maintained at substantially the same time. It is preferred that the thrombin inhibitor and the NSAID be co-administered concurrently on a once-a-day dosing schedule; however, varying dosing schedules, such as the thrombin inhibitor once per day and the NSAID once, twice or more times per day, or the NSAID once per day and the thrombin inhibitor once, twice or more times per day, is also encompassed herein. A single oral dosage formulation comprised of both the thrombin inhibitor and the NSAID is preferred. A single dosage formulation will provide convenience for the patient.

The instant invention also provides pharmaceutical compositions comprised of a therapeutically effective amount of an NSAID, or a pharmaceutically acceptable salt thereof, in combination with a therapeutically effective amount of a thrombin inhibitor, or a pharmaceutically acceptable salt thereof, and a pharmaceutically acceptable carrier. One embodiment of the instant compositions is a single composition adapted for oral administration comprised of a therapeutically effective amount of a COX-2 inhibitor in combination with a therapeutically effective amount of a thrombin inhibitor and a pharmaceutically acceptable carrier. The combination can also be administered in separate dosage forms, each having one of the active agents. If administered in separate dosage forms, the separate dosage forms are administered such that the beneficial effect of each active agent is realized by the patient at substantially the same time.

NSAIDs

Common NSAIDs include salicylates such as aspirin, sodium salicylate, choline salicylate, salicylsalicylic acid, diflunisal, and salsalate; indoleacetic acids such as indomethacin and sulindac; pyrazoles such as phenylbutazone, oxyphenbutazone; pyrrolealkanoic acids such as tolmetin; phenylacetic acids such as ibuprofen, feroprofen, flurbiprofen, and ketoprofen; fenamates such as mefanamic acid, and meclofenamate; oxicams such as piroxicam; and naphthaleneacetic acids such as naproxen. Cyclo-oxygenase inhibitors such as COX-1 and COX-2 inhibitors are also NSAIDs.

COX-2 Inhibitors

Employing the human whole blood COX-1 assay and the human whole blood COX-2 assay described in C. Brideau et al, *Inflamm. Res.* 45: 68–74 (1996), herein incorporated by reference, preferably, the compounds have a cyclooxygenase-2 $IC_{50}$ of less than about 2 $\mu M$ in the human whole blood COX-2 assay, yet have a cyclooxygenase-1 $IC_{50}$ of greater than about 5 $\mu M$ in the human whole blood COX-1 assay. Also preferably, the compounds have a selectivity ratio of cyclooxygenase-2 inhibition over cyclooxygenase-1 inhibition of at least 10, and more preferably of at least 40. The resulting selectivity may indicate an ability to reduce the incidence of common NSAID-induced side effects.

"Inhibitor of cyclooxygenase-2", "cyclooxygenase-2 inhibitor" and "COX-2 inhibitor" as used herein embrace compounds which selectively inhibit cyclooxygenase-2 over cyclooxygenase-1.

The inhibitor of cyclooxygenase-2 may be administered at a dosage level up to conventional dosage levels for NSAIDs. Suitable dosage levels will depend upon the anti-inflammatory effect of the chosen inhibitor of cyclooxygenase-2, but typically suitable levels will be about 0.001 to 50 mg/kg per day, preferably 0.005 to 30mg/kg per day, and especially 0.05 to 10 mg/kg per day. The compound may be administered on a regimen of up to 6 times per day, preferably 1 to 4 times per day, and especially once per day.

As explained in J. Talley, *Exp. Opin. Ther. Patents* (1997), 7(1), pp. 55–62, three distinct structural classes of selective COX-2 inhibitor compounds have been identified. One class is the methane sulfonanilide class of inhibitors, of which NS-398, flosulide, nimesulide and (i) are example members.

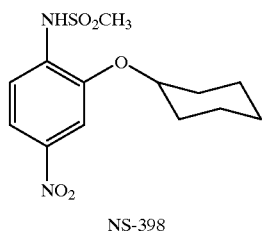

NS-398

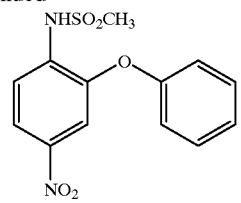

Nimesulide

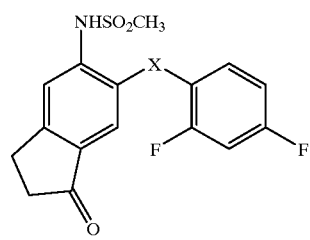

(i), X = S
Flosulide, X = O

A second class is the tricyclic inhibitor class, which can be further divided into the sub-classes of tricyclic inhibitors with a central carbocyclic ring (examples include SC-57666, 1, and 2); those with a central monocyclic heterocyclic ring (examples include DuP 697, SC-58125, SC-58635, and 3, 4 and 5; and those with a central bicyclic heterocyclic ring (examples include 6, 7, 8, 9 and 10). Compounds 3, 4 and 5 are described in U.S. Pat. No. 5,474,995.

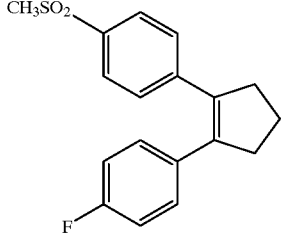

SC-57666

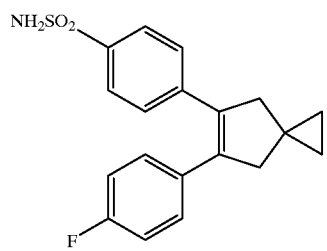

1

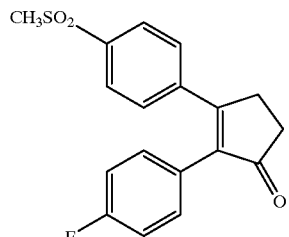

2

DuP 697
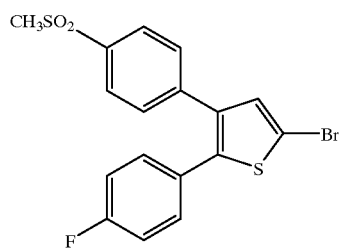
SC-58125
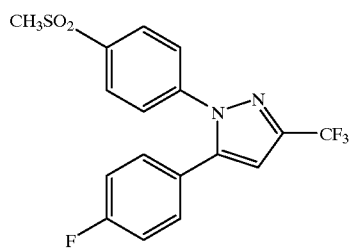
SC-58635
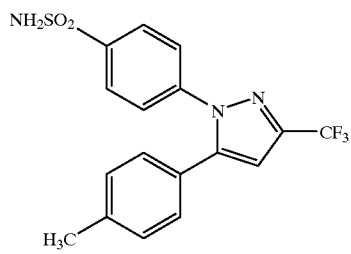
3
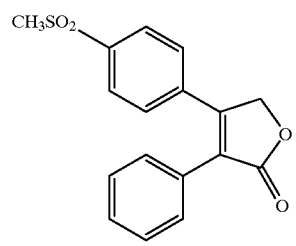
4
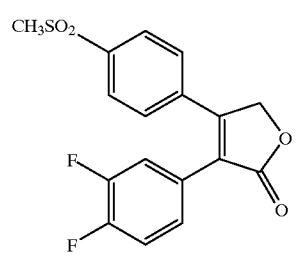
5
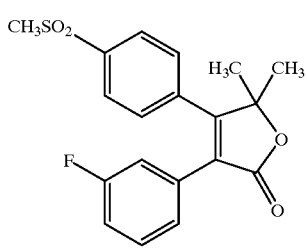
6
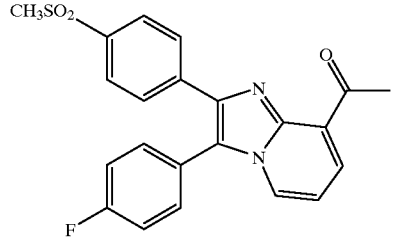
7
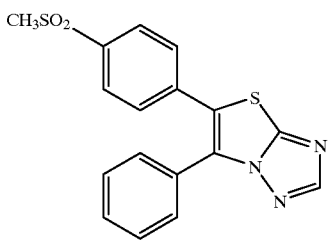
8
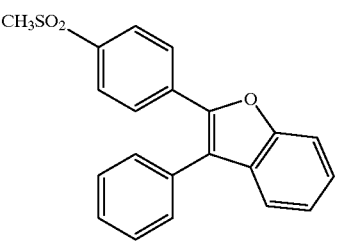
9
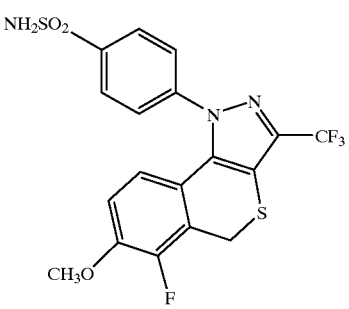
10
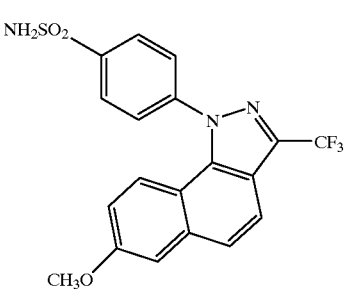
The third identified class can be referred to as those which are structurally modified NSAIDs, and includes 11a and structure 11 as example members.

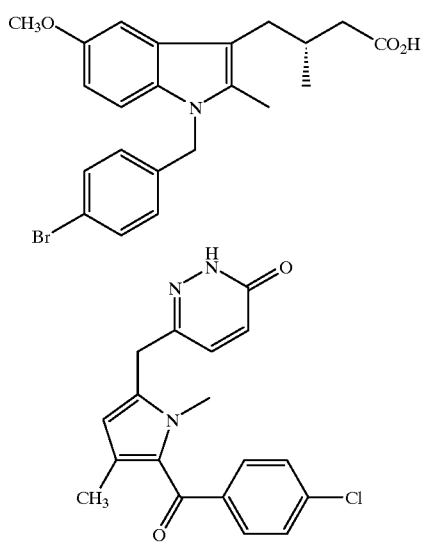

11a

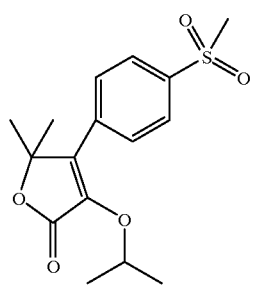

11

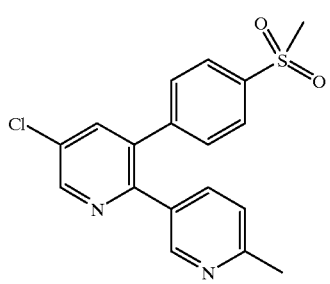

In addition to the structural classes, sub-classes, specific COX-2 inhibitor compound examples, and reference journal and patent publications described in the Talley publication which are all herein incorporated by reference, examples of compounds which selectively inhibit cyclooxygenase-2 have also been described in the following patent publications, all of which are herein incorporated by reference: U.S. Pat. No. 's 5,344,991, 5,380,738, 5,393,790, 5,409,944, 5,434,178, 5,436,265, 5,466,823, 5,474,995, 5,510,368, 5,536,752, 5,550,142, 5,552,422, 5,604,253, 5,604,260, 5,639,780; and International Patent Specification Nos. 94/13635, 94/15932, 94/20480, 94/26731, 94/27980, 95/00501, 95/15316, 96/03387, 96/03388, 96/06840; and International Publication No.'s WO 94/20480, WO 96/21667, WO 96/31509, WO 96/36623, WO 97/14691, WO 97/16435.

Additional COX-2 inhibitor compounds which are included in the scope of this invention include:

12

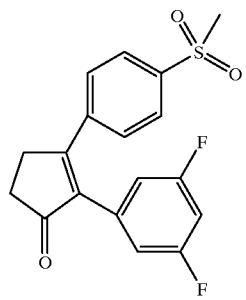

14

13

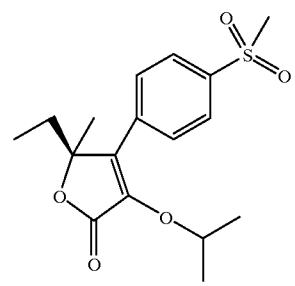

15

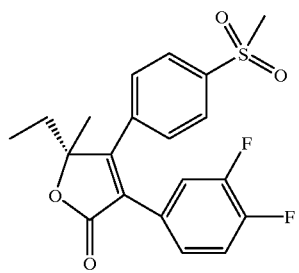

16

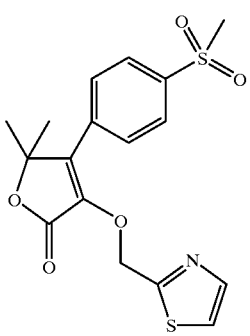

17

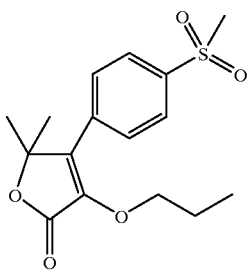

18

17

-continued

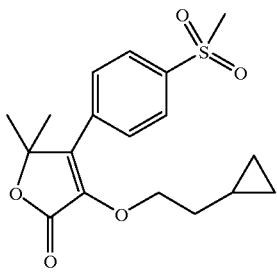

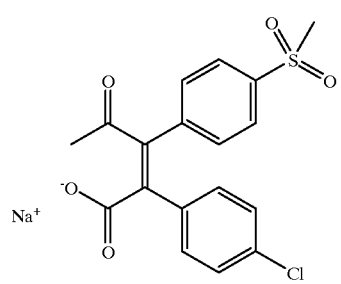

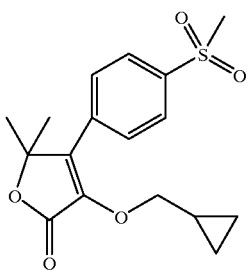

22

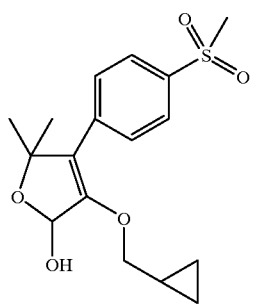

23

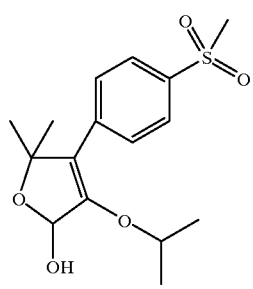

18

-continued

19

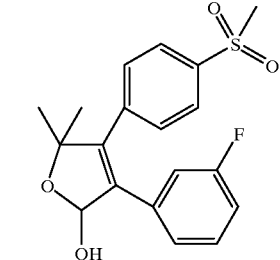

25

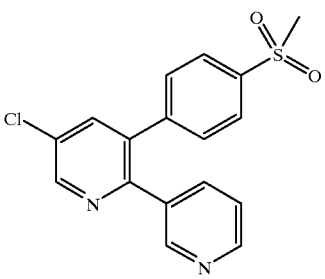

Some of the compounds above can also be identified by the following chemical names:

3:3-phenyl-4-(4-(methylsulfonyl)phenyl)-2-(5H)-furanone U.S. Pat. No. 5,474,995, Ex 23);

4:3-(3,4-difluorophenyl)-4-(4-(methylsulfonyl)phenyl)-2-(5H)-furanone U.S. Pat. No. 5,474,995, Ex 16);

5:5,5-dimethyl-4-(4-(methylsulfonyl)phenyl)-3-(3-fluorophenyl)-5H-furan-2-one U.S. Pat. No. 5,474,995);

12:5,5-dimethyl-4-(4-(methylsulfonyl)phenyl)-3-(2-propoxy)-5H-furan-2-one EP 863 891;

13:5-chloro-3-(4-(methylsulfonyl)phenyl)-2-(2-methyl-5-pyridinyl)pyridine EP 912 518;

14:2-(3,5-difluorophenyl)-3-(4-(methylsulfonyl)phenyl)-2-cyclopenten-1-one EP 754 687;

15:5(S)-5-ethyl-5-methyl-4-(4-(methylsulfonyl)phenyl)-3-(2-propoxy)-5H-furan-2-one EP 863 891;

16:5-ethyl-5-methyl-4-(4-(methylsulfonyl)phenyl)-3-(3,4-difluorophenyl)-5H-furan-2-one EP 754 687;

17:3-((2-thiazolyl)methoxy)-4-(4-(methylsulfonyl)phenyl)-5,5-dimethyl-5H-furan-2-one EP 863 891;

18:3-propyloxy-4-(4-(methylsulfonyl)phenyl)-5,5-dimethyl-5H-furan-2-one EP 863 891;

19:3-(1-cyclopropylethoxy)-5,5-dimethyl-4-(4-methylsulfonyl)phenyl)-5H-furan-2-one EP 863 891;

20:sodium 2-(4-chlorophenyl)-3-(4-(methylsulfonyl)phenyl)-4-oxo-2-pentenoate WO 96/36623;

21:3-(cyclopropylmethoxy)-5,5-dimethyl-4-(4-(methylsulfonyl)phenyl)-5H-furan-2-one EP 863 891;

22:3-(cyclopropylmethoxy)-5,5-dimethyl-4-(4-(methylsulfonyl)phenyl)-2,5-dihydrofuran-2-ol WO 97/16435;

23:3-isopropoxy-5,5-dimethyl-4-(4-(methylsulfonyl)phenyl)-2,5-dihydrofuran-2-ol WO 97/16435;

24:5,5-dimethyl-3-(3-fluorophenyl)-2-hydroxy-4-(4-(methylsulfonyl)phenyl)-2,5-dihydrofuran WO 97/16435;

25:5-Chloro-3-(4-(methylsulfonyl)phenyl)-2-(3-pyridinyl)pyridine WO 98/03484.

The following publications describe and/or provide methods for making the compounds as indicated: compounds 12, 15, 17, 18, 19 and 21, WO 97/14691; compounds 22, 23 and 24, WO 97/16435; compound 20, WO 96/36623; compound 14, U.S. Pat. No. 5,536,752; compound 16, U.S. Pat. No. 5,474,995. See Examples herein for compounds 13 and 25 WO 98/03484.

Also incorporated herein by reference are those compounds described in WO 96/41645 as having structural Formula I, shown below, and the definition and preferred definitions and species described therein:

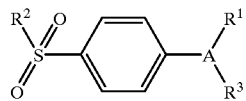

Particularly preferred compounds of formula (I) include:

5-(4-fluorophenyl)-1-[4-(methylsulfonyl)phenyl]-3-(trifluoromethyl)pyrazole;

4-(4-fluorophenyl)-5-[4-(methylsulfonyl)phenyl]-1-phenyl-3-(trifluoromethyl)pyrazole;

4-(5-(4-chlorophenyl)-3-(4-methoxyphenyl)-1H-pyrazol-1-yl)benzenesulfonamide;

4-(3,5-bis(4-methylphenyl)-1H-pyrazol-1-yl)benzenesulfonamide;

4-(5-(4-chlorophenyl)-3-phenyl-1H-pyrazol-1-yl)benzenesulfonamide;

4-(3,5-bis(4-methoxyphenyl)-1H-pyrazol-1-yl)benzenesulfonamide;

4-(5-(4-chlorophenyl)-3-(4-methylphenyl)-1H-pyrazol-1-yl)benzenesulfonamide;

4-(5-(4-chlorophenyl)-3-(4-nitrophenyl)-1H-pyrazol-1-yl)benzenesulfonamide;

4-(5-(4-chlorophenyl)-3-(5-chloro-2-thienyl)-1H-pyrazol-1-yl)benzenesulfonamide;

4-(4-chloro-3,5-diphenyl-1H-pyrazol-1-yl)benzenesulfonamide;

4-(5-(4-chlorophenyl)-3-(trifluoromethyl)-1H-pyrazol-1-yl)benzenesulfonamide;

4-(5-phenyl)-3-(trifluoromethyl)-1H-pyrazol-1-yl)benzenesulfonamide;

4-(5-(4-fluorophenyl)-3-(trifluoromethyl)-1H-pyrazol-1-yl)benzenesulfonamide;

4-(5-(4-methoxyphenyl)-3-(trifluoromethyl)-1H-pyrazol-1-yl)benzenesulfonamide;

4-(5-(4-chlorophenyl)-3-(difluoromethyl)-1H-pyrazol-1-yl)benzenesulfonamide;

4-(5-(4-methylphenyl)-3-(trifluoromethyl)-1H-pyrazol-1-yl)benzenesulfonamide;

4-(4-chloro-5-(4-chlorophenyl)-3-(trifluoromethyl)-1H-pyrazol-1-yl)benzenesulfonamide;

4-(3-(difluoromethyl)-5-(4-methylphenyl)-1H-pyrazol-1-yl)benzenesulfonamide;

4-(3-(difluoromethyl)-5-phenyl-1H-pyrazol-1-yl)benzenesulfonamide;

4-(3-(difluoromethyl)-5-(4-methoxyphenyl)-1H-pyrazol-1-yl)benzenesulfonamide;

4-(3-cyano-5-(4-fluorophenyl)-1H-pyrazol-1-yl)benzenesulfonamide;

4-(3-(difluoromethyl)-5-(3-fluoro-4-methoxyphenyl)1H-pyrazol-1-yl)benzenesulfonamide;

4-(5-(3-fluoro-4-methoxyphenyl)-3-(trifluoromethyl)-1H-pyrazol-1-yl)benzenesulfonamide;

4-(4-chloro-5-phenyl-1H-pyrazol-1-yl)benzenesulfonamide;

4-(5-(4-chlorophenyl)-3-(hydroxyphenyl)-1H-pyrazol-1-yl)benzenesulfonamide;

4-(5-(4-(N,N-dimethylamino)phenyl)-3-(trifluoromethyl)-1H-pyrazol-1-yl)benzenesulfonamide;

5-(4-fluorophenyl)-6-(4-(methylsulfonyl)phenyl)spiro[2.4]hept-5-ene;

4-(6-(4-fluorophenyl)spiro[2.4]hept-5-en-5-yl)benzenesulfonamide;

6-(4-fluorophenyl)-7-(4-(methylsulfonyl)phenyl)spiro[3.4]oct-6-ene;

5-(3-chloro-4-methoxyphenyl)-6-(4-(methylsulfonyl)phenyl)spiro[2.4]hept-5-ene;

4-(6-(3-chloro-4-methoxyphenyl)spiro[2.4]hept-5-en-5-yl)benzenesulfonamide;

5-(3,5-dichloro-4-methoxyphenyl)-6-(4-(methylsulfonyl)phenyl)spiro[2.4]hept-5-ene;

5-(3-chloro-4-fluorophenyl)-6-(4-(methylsulfonyl)phenyl)spiro[2.4]hept-5-ene;

4-(6-(3,4-dichlorophenyl)spiro[2.4]hept-5-en-5-yl)benzenesulfonamide;

2-(3-chloro-4-fluorophenyl)-4-(4-fluorophenyl)-5-(4-methylsulfonylphenyl)thiazole;

2-(2-chlorophenyl)-4-(4-fluorophenyl)-5-(4-methylsulfonylphenyl)thiazole;

5-(4-fluorophenyl)-4-(4-methylsulfonylphenyl)-2-methylthiazole;

4-(4-fluorophenyl)-5-(4-methylsulfonylphenyl)-2-trifluoromethylthiazole;

4-(4-fluorophenyl)-5-(4-methylsulfonylphenyl)-2-(2-thienyl)thiazole;

4-(4-fluorophenyl)-5-(4-methylsulfonylphenyl)-2-benzylaminothiazole;

4-(4-fluorophenyl)-5-(4-methylsulfonylphenyl)-2-(1-propylamino)thiazole;

2-((3,5-dichlorophenoxy)methyl)-4-(4-fluorophenyl)-5-(4-(methylsulfonyl)phenyl)thiazole;

5-(4-fluorophenyl)-4-(4methylsulfonylphenyl)-2-trifluoromethylthiazole;

1-methylsulfonyl-4-(1,1-dimethyl-4-(4-fluorophenyl)cyclopenta-2,4-dien-3-yl)benzene;

4-(4-(4-fluorophenyl)-1,1-dimethylcyclopenta-2,4-dien-3-yl)benzenesulfonamide;

5-(4-fluorophenyl)-6-(4-(methylsulfonyl)phenyl)spiro[2.4]hepta-4,6-diene;

4-(6-(4-fluorophenyl)spiro[2.4]hepta-4,6-dien-5-yl)benzenesulfonamide;

6-(4-fluorophenyl)-2-methoxy-5-(4-(methylsulfonyl)phenyl)-pyridine-3-carbonitrile;

2-bromo-6-(4-fluorophenyl)-5-(4-(methylsulfonyl)phenyl)-pyridine-3-carbonitrile;

6-(4-fluorophenyl)-5-(4-(methylsulfonyl)phenyl)-2-phenyl-pyridine-3-carbonitrile;

4-(2-(4-methylpyridin-2-yl)-4-(trifluoromethyl)-1H-imidazol-1-yl)benzenesulfonamide;

4-(2-(5-methylpyridin-3-yl)-4-(trifluoromethyl)-1H-imidazol-1-yl)benzenesulfonamide;

4-(2-(2-methylpyridin-3-yl)-4-(trifluoromethyl)-1H-imidazol-1-yl)benzenesulfonamide;

3-( 1-(4-(methylsulfonyl)phenyl)-4-(trifluoromethyl)-1H-imidazol-2-yl)benzenesulfonamide;

2-(1-(4-(methylsulfonyl)phenyl)-4-(trifluoromethyl)-1H-imidazol-2-yl)pyridine;

2-methyl-4-(1-(4(methylsulfonyl)phenyl)4-(trifluoromethyl)-1H-imidazol-2-yl)pyridine;

2-methyl-6-(1-(4-(methylsulfonyl)phenyl)-4-(trifluoromethyl)-1H-imidazol-2-yl)pyridine;

4-(2-(6-methylpyridin-3-yl)-4-(trifluoromethyl)-1H-imidazol-1-yl)benzenesulfonamide;

2-(3,4-difluorophenyl)-1-(4-(methylsulfonyl)phenyl)-4-(trifluoromethyl)-1H-imidazole;

4-(2-(4-methylphenyl)-4-(trifluoromethyl)-1H-imidazol-1-yl)benzenesulfonamide;

2-(4-chlorophenyl)-1-(4-(methylsulfonyl)phenyl)-4-methyl-1H-imidazole;

2-(4-chlorophenyl)-1-(4-(methylsulfonyl)phenyl)-4-phenyl-1H-imidazole;

2-(4-chlorophenyl)-4-(4-fluorophenyl)-1-(4-(methylsulfonyl)phenyl)-1H-imidazole;

2-(3-fluoro-4-methoxyphenyl)-1-(4-(methylsulfonyl)phenyl)-4-(trifluoromethyl)-1H-imidazole;

1-(4-(methylsulfonyl)phenyl)-2-phenyl-4-trifluoromethyl-1H-imidazole;

2-(4-methylphenyl)-1-(4(methylsulfonyl)phenyl)4-trifluoromethyl-1H-imidazole;

4-(2-(3-chloro-4-methylphenyl)-4-(trifluoromethyl)-1H-imidazol-1-yl)benzenesulfonamide;

2-(3-fluoro-5-methylphenyl)-1-(4-(methylsulfonylphenyl)-4-(trifluoromethyl)-1H-imidazole;

4-(2-(3-fluoro-5-methylphenyl)-4-(trifluoromethyl)-1H-imidazol-1-yl)benzenesulfonamide;

2-(3-methylphenyl)-1-(4-(methylsulfonyl)phenyl)-4-(trifluoromethyl)-1H-imidazole;

4-(2-(3-methylphenyl)-4-(trifluoromethyl)-1H-imidazol-1-yl)benzenesulfonamide;

1-(4-(methylsulfonyl)phenyl)-2-(3-chlorophenyl)-4-(trifluoromethyl)-1H-imidazole;

4-(2-(3-chlorophenyl)-4-(trifluoromethyl)-1H-imidazol-1-yl)benzenesulfonamide;

4-(2-phenyl-4-(trifluoromethyl)-1H-imidazol-1-yl)benzenesulfonamide;

4-(2-(4-methoxy-3-chlorophenyl)-4-(trifluoromethyl)-1H-imidazol-1-yl)benzenesulfonamide;

1-allyl-4-(4-fluorophenyl)-3-(4-(methylsulfonyl)phenyl)-5-(trifluoromethyl)-1H-pyrazole;

4-(1-ethyl-4-(4-fluorophenyl)-5-(trifluoromethyl)-1H-pyrazol-3-yl)benzenesulfonamide;

N-phenyl-(4-(4-fluorophenyl)-3-(4-(methylsulfonyl)phenyl)-5-(trifluoromethyl)-1H-pyrazol-1-yl)acetamide;

ethyl (4-(4-fluorophenyl)-3-(4-(methylsulfonyl)phenyl)-5-(trifluoromethyl)-1H-pyrazol-1-yl)acetate;

4-(4-fluorophenyl)-3-(4-(methylsulfonyl)phenyl)-1-(2-phenylethyl)-1H-pyrazole;

4-(4-fluorophenyl)-3-(4-(methylsulfonyl)phenyl)-1-(2-phenylethyl)-5-(trifluoromethyl)pyrazole;

1-ethyl-4-(4-fluorophenyl)-3-(4-(methylsulfonyl)phenyl)-5-(trifluoromethyl)-1H-pyrazole;

5-(4-fluorophenyl)-4-(4-(methylsulfonyl)phenyl)-2-(trifluoromethyl)-1H-imidazole;

4-(4-(methylsulfonyl)phenyl)-5-(2-thiophenyl)-2-(trifluoromethyl)-1H-imidazole;

5-(4-fluorophenyl)-2-methoxy-4-(4-(methylsulfonyl)phenyl)-6-(trifluoromethyl)pyridine;

2-ethoxy-5-(4-fluorophenyl)-4-(4-(methylsulfonyl)phenyl)-6-(trifluoromethyl)pyridine;

5-(4-fluorophenyl)-4-(4-(methylsulfonyl)phenyl)-2-(2-propynyloxy)-6-(trifluoromethyl)pyridine;

2-bromo-5-(4-fluorophenyl)-4-(4-(methylsulfonyl)phenyl)-6-(trifluoromethyl)pyridine;

4-(2-(3-chloro-4-methoxyphenyl)-4,5-difluorophenyl)benzenesulfonamide;

1-(4-fluorophenyl)-2-(4-(methylsulfonyl)phenyl)benzene;

5-difluoromethyl-4-(4-(methylsulfonyl)phenyl)-3-phenylisoxazole;

4-(3-ethyl-5-phenylisoxazol-4-yl)benzenesulfonamide;

4-(5-difluoromethyl-3-phenylisoxazol-4yl)benzenesulfonamide;

4-(5-hydroxymethyl-3-phenylisoxazol-4-yl)benzenesulfonamide;

4-(5-methyl-3-phenylisoxazol-4-yl)benzenesulfonamide;

1-(2-(4-fluorophenyl)cyclopenten-1-yl)-4-(methylsulfonyl)benzene;

1-(2-(4-fluoro-2-methylphenyl)cyclopenten-1-yl)-4-(methylsulfonyl)benzene;

1-(2-(4-chlorophenyl)cyclopenten-1-yl)-4-(methylsulfonyl)benzene;

1-(2-(2,4-dichlorophenyl)cyclopenten-1-yl)-4-(methylsulfonyl)benzene;

1-(2-(4-trifluoromethylphenyl)cyclopenten-1-yl)-4-(methylsulfonyl)benzene;

1-(2-(4-methylthiophenyl)cyclopenten-1-yl)-4-(methylsulfonyl)benzene;

1-(2-(4-fluorophenyl)-4,4-dimethylcyclopenten-1-yl)-4-(methylsulfonyl)benzene;

4-(2-(4-fluorophenyl)-4,4-dimethylcyclopenten-1-yl)benzenesulfonamide;

1-(2-(4-chlorophenyl)4,4-dimethylcyclopenten-1-yl)-4-(methylsulfonyl)benzene;

4-(2-(4-chlorophenyl)-4,4-dimethylcyclopenten-1-yl)benzenesulfonamide;

4-(2-(4-fluorophenyl)cyclopenten-1-yl)benzenesulfonamide;

4-(2-(4-chlorophenyl)cyclopenten-1-yl)benzenesulfonamide;

1-(2-(4-methoxyphenyl)cyclopenten-1-yl)4-(methylsulfonyl)benzene;

1-(2-(2,3-difluorophenyl)cyclopenten-1-yl)-4-(methylsulfonyl)benzene;

4-(2-(3-fluoro-4-methoxyphenyl)cyclopenten-1-yl)benzenesulfonamide;

1-(2-(3-chloro-4-methoxyphenyl)cyclopenten-1-yl)-4-(methylsulfonyl)benzene;

4-(2-(3-chloro-4-fluorophenyl)cyclopenten-1-yl)benzenesulfonamide;

4-(2-(2-methylpyridin-5-yl)cyclopenten-1-yl)benzenesulfonamide;

ethyl 2-(4-(4-fluorophenyl)-5-(4-(methylsulfonyl)phenyl)oxazol-2-yl)-2-benzyl-acetate;

2-(4-(4-fluorophenyl)-5-(4-(methylsulfonyl)phenyl)oxazol-2-yl)acetic acid;

2-(tert-butyl)-4-(4-fluorophenyl)-5-(4-(methylsulfonyl)phenyl)oxazole;

4-(4-fluorophenyl)-5-(4-(methylsulfonyl)phenyl)-2-phenyloxazole;

4-(4-fluorophenyl)-2-methyl-5-(4-(methylsulfonyl) phenyl)oxazole; and 4-(5-(3-fluoro-4-methoxyphenyl)-2-trifluoromethyl-4-oxazolyl)benzenesulfonamide; or a pharmaceutically acceptable salt thereof.

The dosage regimen utilizing a thrombin inhibitor in combination with the NSAID is selected in accordance with a variety of factors including type, species, age, weight, sex and medical condition of the patient; the severity of the condition to be treated; the route of administration; the renal and hepatic function of the patient; and the particular compound or salt or ester thereof employed. Since two different active agents are being used together in a combination therapy, the potency of each of the agents and the interactive effects achieved by combining them together must also be taken into account. A consideration of these factors is well within the purview of the ordinarily skilled clinician for the purpose of determining the therapeutically effective or prophylactically effective dosage amounts needed to prevent, counter, or arrest the progress of the condition.

Administration of the drug combination to the patient includes both self-administration and administration to the patient by another person.

Additional active agents may be used in combination with the NSAID and thrombin inhibitor in a single dosage formulation, or may be administered to the patient in a separate dosage formulation, which allows for concurrent or sequential administration. Examples of additional active agents which may be employed include HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors; probucol; niacin; fibrates such as clofibrate, fenofibrate, and gemfibrizol; cholesterol absorption inhibitors; bile acid sequestrants; LDL (low density lipoprotein) receptor inducers; vitamin $B_6$ (also known as pyridoxine) and the pharmaceutically acceptable salts thereof such as the HCl salt; vitamin $B_{12}$ (also known as cyanocobalamin); β-adrenergic receptor blockers; folic acid or a pharmaceutically acceptable salt or ester thereof such as the sodium salt and the methylglucamine salt; and antioxidant vitamins such as vitamin C and E and beta carotene.

The active drugs can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active drugs may also be delivered by the use of monoclonal antibodies as individual carriers to which the compound molecules are coupled. They may also be coupled with soluble polymers as targetable drug carriers. Such polymers can include polyvinyl-pyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, the active drugs may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Although the active agents may be administered in divided doses, for example two or three times daily, a single daily dose of each of the thrombin inhibitor and the NSAID is preferred, with a single daily dose of both agents in a single pharmaceutical composition being most preferred.

An additional embodiment of the instant invention involves a kit comprised of an NSAID such as a COX-2 inhibitor in an oral dosage formulation and a thrombin inhibitor in a separate oral dosage formulation. More particularly, the kit is comprised of a COX-2 inhibitor selected from the group consisting of 5-chloro-3-(4-(methylsulfonyl)phenyl)-2-(2-methyl-5-pyridinyl)pyridine; 2-(3,5-difluorophenyl)-3-(4-(methylsulfonyl)phenyl)-2-cyclopenten-1-one; 3-phenyl-4-(4-(methylsulfonyl)phenyl)-2-(5H)-furanone; 3-(3,4-difluorophenyl)-4-(4-(methylsulfonyl)phenyl)-2-(5H)-furanone; 5,5-dimethyl-4-(4-(methylsulfonyl)phenyl)-3-3-fluorophenyl)-5H-furan-2-one; and the thrombin inhibitor is 3-(2-phenylethylamino)-6-methyl-1-(2-amino-6-methyl-5-methylene-carboxamidomethylpyridinyl)-2-pyridinone. In one class of this embodiment the COX-2 inhibitor is selected from 5-chloro-3-(4-(methylsulfonyl)phenyl)-2-(2-methyl-5-pyridinyl)pyridine; 2-(3,5-difluorophenyl)-3-(4-(methylsulfonyl)phenyl)-2-cyclopenten-1-one; 3-phenyl-4-(4-(methylsulfonyl)phenyl)-2-(5H)-furanone; 3-(3,4-difluorophenyl)-4-(4-(methylsulfonyl)phenyl)-2-(5H)-furanone; 5,5-dimethyl-4-(4-(methylsulfonyl)phenyl)-3-(3-fluorophenyl)-5H-furan-2-one.

One example of this embodiment is a kit comprised of an oral dosage formulation of a COX-2 inhibitor and an oral dosage formulation of a thrombin inhibitor. The packaging for the kit could be designed and manufactured in a variety of ways. A preferred example is a blister package containing rows of a COX-2 inhibitor tablet and a thrombin inhibitor tablet placed side by side on the same blister card, each of the two tablets in its own blister bubble, with calendar or similar type markings on the card that convey to the user that one "pair" of tablets (i.e., one COX-2 inhibitor tablet and one thrombin inhibitor tablet) is to be ingested per day.

Examples of dosage formulations suitable for use in practicing the instant invention follow. In the examples, the COX-2 inhibitor is 3-phenyl-4-(4-(methylsulfonyl)phenyl)-2-(5H)-furanone (except for Example 12 where the COX-2 inhibitor is 3-(3,4-difluorophenyl)-4-(4-(methylsulfonyl) phenyl)-2-(5H)-furanone) and the thrombin inhibitor is 3-(2-phenylethylamino)-6-methyl-1-(2-amino-6-methyl-5-methylene-carboxamidomethylpyridinyl)-2-pyrazinone, N'-[[1-(aminoiminomethyl)-4-piperidinyl]methyl]-N-(3,3-diphenylpropionyl)-L-proline amide, or 3-(2-phenethylamino)-6-methyl-1-(2-amino-6-methyl-5-methylenecarboxamidomethylpyridinyl)-2-pyridinone.

EXAMPLE 4

| Wet granulated tablet composition | |
|---|---|
| Amount per tablet | Ingredient |
| 25 mg | COX-2 inhibitor |
| 79.7 mg | Microcrystalline cellulose |
| 79.7 mg | Lactose monohydrate |
| 6 mg | Hydroxypropyl cellulose |
| 8 mg | Croscarmellose sodium |
| 0.6 mg | Iron oxide |
| 1 mg | Magnesium stearate |

Tablet dose strengths of between 5 and 125 mg can be accommodated by varying total tablet weight, and the ratio of the first three ingredients. Generally it is preferable to maintain a 1:1 ratio for microcrystalline cellulose: lactose monohydrate.

EXAMPLE 4A

Wet granulated tablet composition

| Amount per tablet | Ingredient |
|---|---|
| 12.5 mg | COX-2 inhibitor |
| 86 mg | Microcrystalline cellulose |
| 86 mg | Lactose monohydrate |
| 6 mg | Hydroxypropyl cellulose |
| 8 mg | Croscarmellose sodium |
| 0.6 mg | Iron oxide |
| 1 mg | Magnesium stearate |

EXAMPLE 4B

Wet granulated tablet composition

| Amount per tablet | Ingredient |
|---|---|
| 10 mg | COX-2 inhibitor |
| 87.2 mg | Microcrystalline cellulose |
| 87.2 mg | Lactose monohydrate |
| 6 mg | Hydroxypropyl cellulose |
| 8 mg | Croscarmellose sodium |
| 0.6 mg | Iron oxide |
| 1 mg | Magnesium stearate |

EXAMPLE 4C

Wet granulated tablet composition

| Amount per tablet | Ingredient |
|---|---|
| 5 mg | COX-2 inhibitor |
| 89.7 mg | Microcrystalline cellulose |
| 89.7 mg | Lactose monohydrate |
| 6 mg | Hydroxypropyl cellulose |
| 8 mg | Croscarmellose sodium |
| 0.6 mg | Iron oxide |
| 1 mg | Magnesium stearate |

EXAMPLE 5

Directly compressed tablet composition

| Amount per tablet | Ingredient |
|---|---|
| 25 mg | COX-2 inhibitor |
| 106.9 mg | Microcrystalline cellulose |
| 106.9 mg | Lactose anhydrate |
| 7.5 mg | Croscarmellose sodium |
| 3.7 mg | Magnesium stearate |

Tablet dose strengths of between 5 and 125 mg can be accommodated by varying total tablet weight, and the ratio of the first three ingredients. Generally it is preferable to maintain a 1:1 ratio for microcrystalline cellulose: lactose monohydrate.

EXAMPLE 5A

Directly compressed tablet composition

| Amount per tablet | Ingredient |
|---|---|
| 12.5 mg | COX-2 inhibitor |
| 113.2 mg | Microcrystalline cellulose |
| 113.2 mg | Lactose anhydrate |
| 7.5 mg | Croscarmellose sodium |
| 3.7 mg | Magnesium stearate |

EXAMPLE 5B

Directly compressed tablet composition

| Amount per tablet | Ingredient |
|---|---|
| 10 mg | COX-2 inhibitor |
| 42.5 mg | Microcrystalline cellulose |
| 42.5 mg | Lactose anhydrate |
| 4 mg | Croscarmellose sodium |
| 1 mg | Magnesium stearate |

EXAMPLE 5C

Directly compressed tablet composition

| Amount per tablet | Ingredient |
|---|---|
| 5 mg | COX-2 inhibitor |
| 45 mg | Microcrystalline cellulose |
| 45 mg | Lactose anhydrate |
| 4 mg | Croscarmellose sodium |
| 1 mg | Magnesium stearate |

EXAMPLE 6

Hard gelatin capsule composition

| Amount per capsule | Ingredient |
|---|---|
| 25 mg | COX-2 inhibitor |
| 37 mg | Microcrystalline cellulose |
| 37 mg | Lactose anhydrate |
| 1 mg | Magnesium stearate |
| 1 capsule | Hard gelatin capsule |

Capsule dose strengths of between 1 and 50 mg can be accommodated by varying total fill weight, and the ratio of the first three ingredients. Generally it is preferable to maintain a 1:1 ratio for microcrystalline cellulose: lactose monohydrate.

EXAMPLE 7

| Oral solution | |
|---|---|
| Amount per 5 mL dose | Ingredient |
| 50 mg | COX-2 inhibitor |
| to 5 mL with Polyethylene oxide 400 | |

Solution dose strengths of between 1 and 50 mg/5mL can be accommodated by varying the ratio of the two ingredients.

EXAMPLE 8

| Oral suspension | |
|---|---|
| Amount per 5 mL dose | Ingredient |
| 101 mg | COX-2 inhibitor |
| 150 mg | Polyvinylpyrrolidone |
| 2.5 mg | Poly oxyethylene sorbitan monolaurate |
| 10 mg | Benzoic acid |
| to 5 mL with sorbitol solution (70%) | |

Suspension dose strengths of between 1 and 50 mg/5ml can be accommodated by varying the ratio of the first two ingredients.

EXAMPLE 9

| Intravenous infusion | |
|---|---|
| Amount per 200 mL dose | Ingredient |
| 1 mg | COX-2 inhibitor |
| 0.2 mg | Polyethylene oxide 400 |
| 1.8 mg | Sodium chloride |
| to 200 mL | Purified water |

EXAMPLE 10

Combination Tablet Preparation
Tablets containing 25.0, 50.0, and 100.0 mg, respectively, of thrombin inhibitor and 25 mg COX-2 Inhibitor are prepared as illustrated below:

| | Amount-mg | | |
|---|---|---|---|
| Thrombin inhibitor | 25.0 | 50.0 | 100.0 |
| COX-2 inhibitor | 25.0 | 25.0 | 25.0 |
| Microcrystalline cellulose | 37.25 | 100.0 | 175.0 |
| Modified food corn starch | 37.25 | 4.25 | 8.5 |
| Magnesium stearate | 0.50 | 0.75 | 1.5 |

Both active compounds, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of thrombin inhibitor per tablet, and 25 mg COX-2 inhibitor, per tablet.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

EXAMPLE 11

Development and severity of adjuvant-induced arthritis in female Lewis rats

The thrombin inhibitor 3-(2-phenylethylamino)-6-methyl-1-(2-amino-6-methyl-5-methylene-carboxamidomethylpyridinyl)-2-pyrazinone was evaluated to determine its effect on induced arthritis. Arthritis was induced by injection of female Lewis rats with *Mycobacterium butyricum*. The effect of the thrombin inhibitor was compared with the effect of Indomethacin and the effect of a vehicle control.

Fifty 7.5 week old female Lewis rats (body weight 149–174 grams) were included in the study. Forty rats were each injected with an emulsion containing 0.5 mg of *Mycobacterium butyricum* in 0.1 ml of light mineral oil, and a negative control group of 10 rats was not injected with adjuvant.

Ten of the rats receiving *Mycobacterium butyricum* further received Indomethacin by oral gavage at a total daily dose of 1 mg/kg. Ten of the rats receiving *Mycobacterium butyricum* further received the thrombin inhibitor by oral gavage at a total daily dose of 50 mg/kg. Twenty of the rats receiving *Mycobacterium butyricum* further received a vehicle control of sterile distilled water.

Body weights, primary and secondary paw volumes, and lateral radiographs were determined before and at various time points including 21 days following adjuvant injection. Th primary paw was injected with the *Mycobacterium butyricum* while the secondary (contralateral) paw not injected. Paw volumes were determined by mercury displacement plethysmography. Lateral radiographs were obtained under Ketamine and Xylazine anesthesia.

Radiographs were made of both hind paws on days 0 and 21 and evaluated for changes in the soft and hard tissues. The following radiographic changes were graded numerically according to severity: increased soft tissue volume (0–4), narrowing or widening of joint spaces (0–5), subchondral erosion (0–3), periosteal reaction (0–4), osteolysis (0–4), subluxation (0–3), and degenerative joint changes (0–3). The maximum possible score for each foot was 26. High scores correspond with high levels of inflammation.

The foot volumes of the primary paws of all rats injected with *Mycobacterium butyricum* were greater than those of uninduced rats. The foot volumes of the secondary paws of all rats injected with *Mycobacterium butyricum* were also greater than those of uninduced rats. The data show that the thrombin inhibitor had a significant anti-inflammatory effect on the secondary paw, but an insignificant effect on the primary paw.

|  | Increase in primary foot volume | |
| --- | --- | --- |
| Treatment | Day 14 µL | Day 21 µL |
| Uninduced rats | 33 ± 29 | 59 ± 33 |
| Vehicle control | 1579 ± 370 | 2227 ± 592 |
| Thrombin inhibitor | 1591 ± 318 | 1997 ± 605 |
| Indomethacin | 726 ± 174 | 622 ± 156 |
| Uninduced rats | 42 ± 26 | 52 ± 26 |
| Vehicle control | 925 ± 462 | 1266 ± 583 |
| Thrombin inhibitor | 382 ± 312 | 704 ± 289 |
| Indomethacin | 246 ± 162 | 253 ± 138 |

The radiographic total scores for both hind paws of vehicle treated rats were significantly greater than those of uninduced rats on day 21. The radiographic total scores on day 21 for both the primary and secondary paws of rats administered Indomethacin and the secondary paws of rats administered thrombin inhibitor were significantly less than those of the vehicle treated rats.

|  | Radiographic scores | |
| --- | --- | --- |
| Treatment | Primary paws | Secondary paws |
| Uninduced rats | 0 | 0 |
| Vehicle control | 15.3 ± 3.0 | 12.8 ± 3.1 |
| Thrombin inhibitor | 14.0 ± 3.3 | 3.8 ± 3.79 |
| Indomethacin | 4.6 ± 1.6 | 3.5 ± 1.4 |

The data indicate that thrombin inhibitors are useful for treating inflammatory disease and for inhibiting inflammatory response in patients. The data also indicate that thrombin inhibitors are useful for inhibiting secondary inflammatory response in patients developing inflammation induced at a primary site.

EXAMPLE 12

Development and severity of adjuvant-induced arthritis in female Lewis rats using a thrombin inhibitor in combination with a COX-2 inhibitor The thrombin inhibitor 3-(2-phenylethylamino)-6-methyl-1-(2-amino-6-methyl-5-methylene-carboxamidomethylpyridinyl)-2-pyrazinone is evaluated in combination with the COX-2 inhibitor 3-(3,4-difluorophenyl)-4-(4-(methylsulfonyl)phenyl)-2-(5H)-furanone to determine their combined effect on induced arthritis. Arthritis is induced by injection of female Lewis rats with *Mycobacterium butyricum*. The effect of the combination therapy is compared with the effect of Indomethacin, the effect of a vehicle control, the effect of 3-(2-phenylethylamino)-6-methyl-1-(2-amino-6-methyl-5-methylene-carboxamidomethylpyridinyl)-2-pyrazinone alone, and the effect of 3-(3,4-difluorophenyl)-4-(4-(methylsulfonyl)phenyl)-2-(5H)-furanone alone.

Female Lewis rats (body weight 149–174 grams) are included in the study. The rats are each injected with an emulsion containing 0.5 mg of *Mycobacterium butyricum* in 0.1 ml of light mineral oil.

A selected number of rats receiving *Mycobacterium butyricum* further receive a therapeutically effective dose of 3-(2-phenylethylamino)-6-methyl-1-(2-amino-6-methyl-5-methylene-carboxamidomethylpyridinyl)-2-pyrazinone by oral gavage and a therapeutically effective dose of 3-(3,4-difluorophenyl)-4-(4-(methylsulfonyl)phenyl)-2-(5H)-furanone by oral gavage on a daily basis.

What is claimed is:

1. A method for treating a chronic inflammatory disease in a patient which comprises treating the patient with an oral composition comprising a thrombin inhibitor wherein the thrombin inhibitor is selected from the group consisting of 3-(2-phenylethylamino)-6-methyl-1-(2-amino-6-methyl-5-methylene-carboxamidomethylpyridinyl)-2-pyrazinone, N'-[[1-(Aminoiminomethyl)-4-piperidinyl]methyl]-N-(3,3-diphenylpropionyl)-L-proline amide, and 3-(2-phenethylamino)-6-methyl-1-(2-amino-6-methyl-5-methylenecarboxamidomethyl-pyridinyl)-2-pyridinone or a pharmaceutically acceptable salt thereof.

2. A method for treating an inflammatory disease in a patient which comprises treating the patient with an oral composition comprising a thrombin inhibitor and a COX-2 inhibitor.

3. A method of claim 2 wherein the inflammatory disease is selected from the group consisting of nephritis, systemic lupus erythematosus, rheumatoid arthritis, glomerulonephritis, and sarcoidosis.

4. A method of claim 2 wherein the thrombin inhibitor is selected from the group consisting of 3-(2-phenylethylamino)-6-methyl-1-(2-amino-6-methyl-5-methylene-carboxamidomethylpyridinyl)-2-pyrazinone, N'-[[1-(aminoiminomethyl)-4-piperidinyl]methyl]-N-(3,3-diphenylpropionyl)-L-proline amide, and 3-(2-phenethylamino)-6-methyl-1-(2-amino-6-methyl-5-methylenecarboxamidomethylpyridinyl)-2-pyridinone.

5. A method of claim 4 wherein the COX-2 inhibitor is 3-(3,4-difluorophenyl)-4-(4-(methylsulfonyl)phenyl)-2-(5H)-furanone or a pharmaceutically acceptable salt thereof.

6. A method of claim 4 wherein the COX-2 inhibitor is 3-phenyl-4-(4-(methylsulfonyl)phenyl)-2-(5H)-furanone or a pharmaceutically acceptable salt thereof.

7. A method for inhibiting secondary chronic inflammation in a patient developing inflammation at a primary site which comprises treating the patient with a composition comprising an oral thrombin inhibitor.

* * * * *